US00PP32081P3

(12) United States Plant Patent
Lovengreen Ferreira

(10) Patent No.: US PP32,081 P3
(45) Date of Patent: Aug. 18, 2020

(54) ***ARISTOTELIA* PLANT NAMED 'AZ50'**

(50) Latin Name: *Aristotelia chilensis*
Varietal Denomination: AZ50

(71) Applicant: Royal Super Fruits B.V., Katwijk aan Zee (NL)

(72) Inventor: Axel Lovengreen Ferreira, Pitrufquen (CL)

(73) Assignee: ROYAL SUPER FRUITS B.V., Katwijk aan Zee (NL)

( * ) Notice: Subject to any disclaimer, the term of this patent is extended or adjusted under 35 U.S.C. 154(b) by 0 days.

(21) Appl. No.: 16/602,061

(22) Filed: Jul. 29, 2019

(65) Prior Publication Data

US 2020/0037485 P1 Jan. 30, 2020

(30) Foreign Application Priority Data

Jul. 30, 2018 (QZ) ..... PBR 2018/1980

(51) Int. Cl.

| | |
|---|---|
| ***A01H 5/00*** | (2018.01) |
| ***A01H 6/00*** | (2018.01) |
| ***A01H 5/12*** | (2018.01) |

(52) U.S. Cl.

USPC ..... Plt./216

CPC ..... *A01H 6/00* (2018.05); *A01H 5/12* (2013.01)

(58) Field of Classification Search

USPC ..... Plt./216

See application file for complete search history.

*Primary Examiner* — Susan McCormick Ewoldt

*Assistant Examiner* — Karen M Redden

(74) *Attorney, Agent, or Firm* — Penny J. Aguirre

(57) ABSTRACT

A new cultivar of *Aristotelia chilensis* plant named 'AZ50' that is characterized by its vigorous plant habit, its wide and open plant shape and its slightly glossy leaves that are dark green in color.

2 Drawing Sheets

Botanical Classification: *Aristotelia chilensis.*
Varietal Denomination: 'AZ50'.

CROSS REFERENCE TO RELATED APPLICATIONS

This application is co-pending with U.S. Plant Patent Applications filed for a plant derived from the same breeding program that are entitled *Aristotelia* Plant Named 'Pretoria' (U.S. Plant patent application Ser. No. 16/602,063), *Aristotelia* Plant Named 'Sobresale' (U.S. Plant patent Ser. No. 16/602,062), and *Aristotelia* Plant Named 'VB1 (U.S. Plant patent Ser. No. 16/602,064).

BACKGROUND OF THE INVENTION

The present invention relates to a new and distinct cultivar of *Aristotelia chilensis* and will be referred to hereafter by its cultivar name, 'AZ50'. 'AZ50' represents a perennial evergreen shrub grown for landscape use.

'AZ50' was discovered by the Inventor as a chance seedling in a trial field in Pitrufquen, IX region de la Araucanía, Chile in January of 2013. The field had been planted with numerous unnamed proprietary seedling plants from the Inventor's breeding program. The parentage is therefore unknown.

Asexual propagation of the new cultivar was first accomplished by softwood stem cuttings by the Inventor in summer of 2014 in Pitrufquen, IX region de la Araucanía, Chile. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'AZ50' as a unique cultivar of *Aristotelia chilensis.*

1. 'AZ50' exhibits a vigorous plant habit.
2. 'AZ50' exhibits a relatively wide and open plant habit.
3. 'AZ50' exhibits slightly glossy leaves that are dark green in color.

'AZ50' can be compared to the *Aristotelia chilensis* cultivars 'Variegata' (not patented), 'Pretoria', 'Sobresale', and 'VB1'. 'Variegata' differs from 'AZ50' in having a narrow and less open plant habit and variegated foliage. 'Pretoria' differs from 'AZ50' in having a slightly narrower plant shape, young foliage that is green (yellow-green in 'AZ50') and mature foliage that is blue-green in color. 'Sobresale' differs from 'AZ50' in having a narrower plant shape, more glossy foliage and darker green foliage. 'VB1' differs from 'AZ50' in having a less open plant habit, a narrower plant shape, branches that are more yellow-green in color, young leaves that are less yellow-green in color and mature foliage that is blue-green in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date.

BRIEF DESCRIPTION OF THE DRAWINGS

The accompanying colored photographs illustrate the overall appearance and distinct characteristics of the new

*Aristotelia*. The photographs were taken of a 24-month-old plant (after a single pruning 3 weeks prior) of 'AZ50' as grown in an unheated greenhouse in a 30-cm container in Boskoop, The Netherlands.

Figure 1:
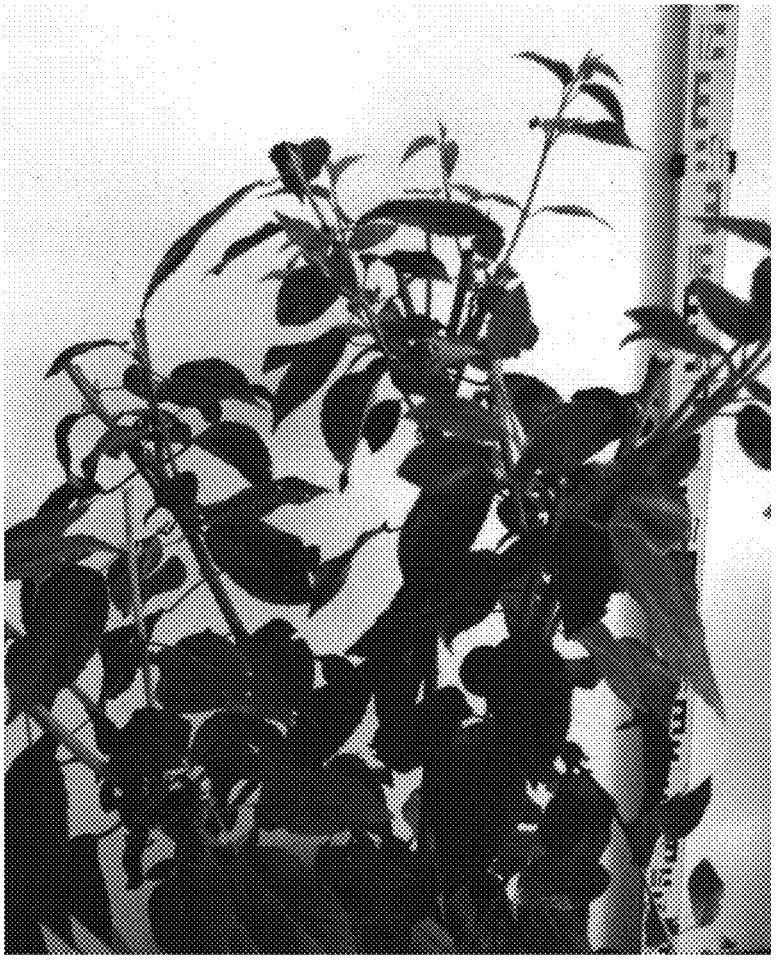
Figure 2:
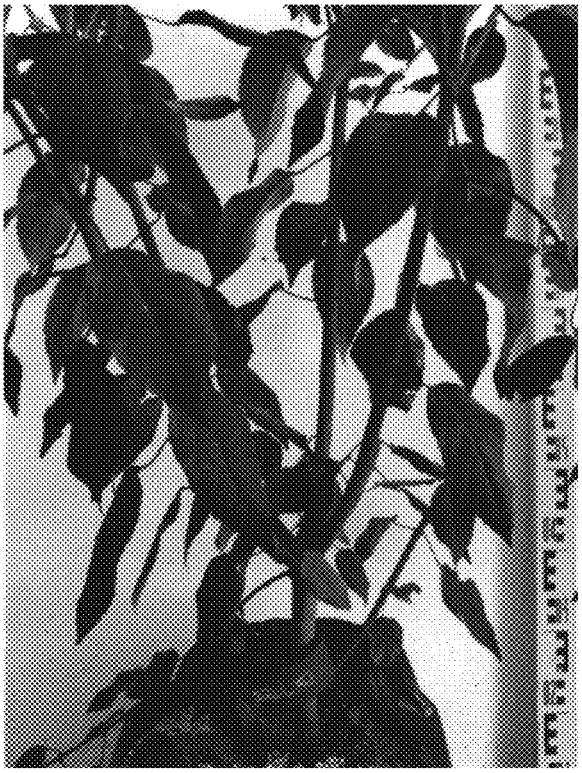

The photograph in FIG. 1 and FIG. 2. provide a view of the plant habit of 'AZ50'.

Figure 3:
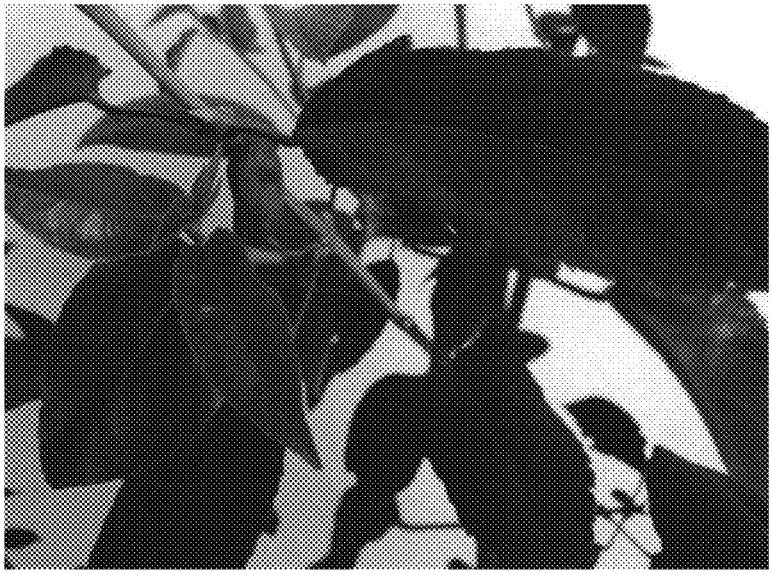

The photograph in FIG. 3 provides a close-up view of the foliage of 'AZ50'.

The colors in the photographs are as close as possible with the photographic and printing technology utilized and the color values cited in the detailed botanical description accurately describe the colors of the new *Aristotelia*.

BOTANICAL DESCRIPTION OF THE PLANT

The following is a detailed description of 24-month-old plants of 'AZ50' as grown in an unheated greenhouse in 30-cm containers in Noordwijkerhout, The Netherlands (with a single pruning 3 weeks prior). The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Plant type.*—Perennial, evergreen shrub.

*Plant habit.*—Broadly obovate.

*Height and spread.*—An average of 98.5 cm in in height and 85.8 cm in spread, reaches 3 m in height and spread as a mature plant in the landscape.

*Cold hardiness.*—At least in U.S.D.A. Zone 8.

*Diseases and pests.*—No susceptibility and resistance to diseases or pests has been observed.

*Root description.*—Fine and fibrous.

*Propagation.*—Softwood stem cuttings.

*Root development.*—An average of 60 days for root initiation with a young rooted plant produced in an average of 4 months.

*Growth rate and vigor.*—Vigorous.

Stem description:

*Stem shape.*—Rounded.

*Stem strength.*—Strong.

*Stem color.*—Young; 146C, mature; 146B to 146C, occasionally tinged with 200C and 200D, internodes; 146B to 146C, old bark; NN137D.

*Stem size.*—An average of 35.8 cm in length and 3 mm in diameter.

*Stem surface.*—Young and mature; Moderately glossy and covered with a very thin wax layer, N189D in color, old bark; densely covered with lenticels; an average of 2 mm in length, 1 mm in width and 157A in color.

*Stem aspect.*—Average angle of vertical to 55° , varying between 30° and 80°.

*Internode length.*—An average of 2.9 cm.

*Branching.*—Freely branching with an average of 1 main branch and 20 lateral branches.

Foliage description:

*Leaf shape.*—Ovate to narrow ovate.

*Leaf arrangement.*—Opposite to near opposite and alternate.

*Leaf aspect.*—Moderately undulate.

*Leaf division.*—Simple.

*Leaf base.*—Obtuse to acute.

*Leaf apex.*—Acute to bluntly acute.

*Leaf margins.*—Serrate.

*Leaf venation.*—Pinnate, color; upper surface 148D, lower surface 145A to 145B.

*Leaf size.*—An average of 12.2 cm in length and 5.7 cm in width.

*Leaf attachment.*—Petiolate.

*Leaf number.*—An average of 26 (13 pairs).

*Leaf surface.*—Upper surface; slightly glossy and very slightly rugose, lower surface; slightly glossy and slightly rugose.

*Leaf color.*—Young foliage; upper surface between 152C and 153A, young lower surface 142C, mature foliage; upper surface between 147A and N189A, mature lower surface NN137C to NN137D.

*Petioles.*—An average of 3.8 cm in length and 1.75 mm in diameter, strong, upper surface color 178A, lower surface color 178A and slightly tinged with 144C, both surfaces slightly glossy and slightly to moderately pubescent, average of 0.2 mm in length and too small to measure color.

Inflorescence description: No flower production.

Fruit and seed: No production observed to date.

It is claimed:

1. A new and distinct cultivar of *Aristotelia* plant named 'AZ50' substantially as herein illustrated and described.

* * * * *